(12) United States Patent
Chawla (10) Patent No.: US 9,248,018 B2
(45) Date of Patent: Feb. 2, 2016

(54) VALVE REPAIR DEVICE

(71) Applicant: Surendra K. Chawla, West Hartford, CT (US)

(72) Inventor: Surendra K. Chawla, West Hartford, CT (US)

(*) Notice: Subject to any disclaimer, the term of this patent is extended or adjusted under 35 U.S.C. 154(b) by 104 days.

(21) Appl. No.: 14/039,568

(22) Filed: Sep. 27, 2013

(65) Prior Publication Data
US 2015/0094800 A1 Apr. 2, 2015

(51) Int. Cl.
*A61F 2/24* (2006.01)

(52) U.S. Cl.
CPC .................... *A61F 2/2457* (2013.01)

(58) Field of Classification Search
CPC .................................... A61F 2/2454
See application file for complete search history.

(56) References Cited

U.S. PATENT DOCUMENTS

| 6,726,706 B2* | 4/2004 | Dominguez ....... A61B 17/0466 606/148 |
| 2013/0053951 A1* | 2/2013 | Ruyra Baliarda ............ 623/2.36 |

* cited by examiner

*Primary Examiner* — Thomas J Sweet
*Assistant Examiner* — Wade P Schutte
(74) *Attorney, Agent, or Firm* — Cantor Colburn LLP (57) ABSTRACT

A valve repair device and method of repair for the mitral valve of the heart is disclosed. The valve repair device includes a leaflet portion, a muscle portion, and a plurality of chords connecting the leaflet portion to the muscle portion. The leaflet portion includes a plurality of partition members to assist the surgeon in sizing the repair device to the patient. A single partition member may form the leaflet portion. Alternatively, multiple partition members may form the leaflet portion. A partition member may include predetermined openings for the attachment of a suture.

10 Claims, 7 Drawing Sheets

VALVE REPAIR DEVICE

BACKGROUND OF THE INVENTION

The present disclosure relates to a valve repair device and a method for repairing a heart valve. More particularly, this disclosure relates to a valve repair device useful in the repair of the mitral valve.

The human heart has four chambers and four one way valves. The right upper chamber, known as the right atrium, receives deoxygenated blood from the body and passes the blood to the right lower chamber, known as the right ventricle, through the tricuspid valve. The blood then passes through the pulmonary valve and is carried via the pulmonary arteries to the lungs for oxygenation. After the blood is oxygenated, it is received into the left side of the heart. The upper chamber, known as the left atrium, receives the blood from the lungs by four pulmonary veins, two from each lung. The blood is then passed to the left ventricle through the mitral valve. The main pumping chamber, the left ventricle, then pushes the blood to the body through the aortic valve.

The mitral valve is also known as a bicuspid valve, as it has two cusps or leaflets. The leaflets consist of the anterior leaflet, which is located adjacent to the aortic valve, and the posterior leaflet. The anterior leaflet is larger than the posterior leaflet. At the junction of the leaflets, each leaflet has a scalloped edge with three rounded portions, known as $A_1$, $A_2$, and $A_3$ for the anterior leaflet, and $P_1$, $P_2$ and $P_3$ for the posterior leaflet. The leaflets are attached to the papillary muscles by the chordae tendineae. The papillary muscles maintain the integrity of chordal leaflet alignment, preventing prolapse of the leaflets. The mitral valve allows blood to flow from the left atrium to the left ventricle but prevents blood from flowing back to the left atrium.

The tricuspid valve and the pulmonary valves are usually less affected by the disease process. Disease in the mitral valve and the aortic valve is more common in the affected adult population.

Mitral valve stenosis, for example, consists of an obstructive lesion to the leaflets of the valve. When the valves are narrow, also called "stenotic" valves, there is an obstruction to the flow of blood to the receiving chamber and an associated back up of blood. Dilatation of the left atrium develops and may be followed by right-sided heart failure and pulmonary edema, causing lung congestion and symptoms of shortness of breath. If the symptoms are severe, surgical intervention may be warranted.

Thickening and calcification is the commonest cause of narrowing of the mitral valve, secondary to the long-term effects of rheumatic disease. The incidence of mitral stenosis has decreased in the United States as the incidence of rheumatic fever has decreased as a result of the early institution of antibiotics. However, the leaking valve or the regurgitant valve incidence has increased in the last two decades. Mitral regurgitation is commonly due to degeneration or myxomatous disease leading to the lack of coaptation of the two mitral leaflets. The lack of coaptation in turn leads to the blood being regurgitated into the left upper chamber or the left atrium, causing pulmonary congestion and shortness of breath. Other causes include rupture of the chordae tendinea or the papillary muscles which are primarily needed to the support the two leaflets. Infection leading to the destruction of the valve leaflet or congenital clefts can also cause mitral regurgitation.

Treatments for these conditions have varied. Opening of the mitral valve was initiated in the 1950's in a closed method, known as a closed commisurotomy (separation of commisures by dialators). With the advent of heart-lung machine in 1955-56 by Dr. John H. Gibbons, Jr., open mitral commisurotomy was started with success.

Due to the high recurrence of stenosis, mitral valve replacement with prosthetic valves, typically constructed of a "ball and cage" (or ball valve), became the normal procedure in the 1960's, as proposed by Dr. Albert Starr. These valves were met with limited success as blood flow obstruction occurred with some frequency, leading to thromboembolism, causing strokes. Other attempts to replace the mitral valve were met with limited success. For example, Bjork Shiley valves were introduced as tilting disc valves to decrease the blood flow obstruction, but a flaw in the design led to strut fracture and their discontinuation. St. Jude valves, with a double tilting disc design, were introduced in the late 1970's. These valves have stood the test of durability and acceptable thromboembolism and are the preferred prosthetic valve replacement in the younger population.

Bioprothesis valves, harvested from heterologous mammals, such as swine and bovine, have also been successfully employed, however, such valves frequently wear out due to degeneration and calcification. Moreover, the current designs for the mitral valve are somewhat limited due to the specific VORTEX flow of the left ventricle. U.S. Pat. No. 6,074,417 illustrates a total bioprosthesis mitral valve.

When possible, surgical repair of the defective valve is preferable over the prosthetic replacement. The thrust of surgical repair has been to preserve the integrity of the papillary muscle, the chordae tendineae and the leaflets. Numerous studies have proved this hypothesis in terms of long-term results and the avoidance of anticoagulation, which can cause life-threatening bleeding complications. In the 1980's, Dr. A F Carpentier of France, pioneered several methods to repair the mitral valve. Rupture of the chordae or the prolapse of the middle scallop of the posterior leaflet was easily repaired by excising the diseased piece and suturing the remaining leaflets. This procedure has become a preferred method and has produced consistent results. These repairs are supported by the placement of a cloth-covered metallic ring to bring the annulus to the near normal level.

Despite the advancement in the surgical management of the posterior leaflet, the repair of the anterior mitral leaflet has proven more difficult. Various surgical techniques have been devised, but without consistent results. Triangular resection of the leaflet, transposing part of the posterior leaflet to the anterior leaflet, chordal shortening have been proposed. Recently the use of the prosthetic material "goretex" sutures have been used as artificial chordae, with some early success. Long Term Results of Mitral Valve Repair for Myxomatous Disease with and without Chordal Replacement with Expanded Polytetrafluoroethylee, The Journal of Thoracic and Cardiovascular Surgery, June 1998, 1279-1286.

The use of prosthetic sutures for the anterior or posterior leaflet requires a great deal of skill on the part of the surgeon to make sure the sutures, duplicating the chords, are of the appropriate length. Moreover, attachment of the sutures to the leaflets and papillary muscles is delicate and cumbersome.

In U.S. Pat. No. 6,997,950, a valve repair device is disclosed that includes a leaflet portion, a muscle portion, and a plurality of chords connecting the leaflet portion to the muscle portion that can be sutured in place to effectuate a repair of the mitral valve.

In U.S. application Ser. No. 2013-0013056-A1, which is incorporated herein by reference, a valve repair instrument and method of repair for the mitral valve of the heart is disclosed. The valve repair instrument includes an elongated body having two ends. One of the ends being configured to maintain a muscle portion of a valve repair device in an expanded position for attachment to the papillary muscle, the other end being configured to maintain a leaflet portion of a valve repair device in an expanded position for attachment to a valve leaflet. The valve repair device is attached to the diseased valve by suturing the leaflet portion to the affected leaflet and suturing the muscle portion to the affected muscle.

BRIEF SUMMARY OF THE INVENTION

A valve repair device and method of repair for the mitral valve of the heart is disclosed. The valve repair device includes a leaflet portion, a muscle portion, and a plurality of chords connecting the leaflet portion to the muscle portion. The leaflet portion includes a plurality of partition members to assist the surgeon in sizing the repair device to the patient. A single partition member may form the leaflet portion. Alternatively, multiple partition members may form the leaflet portion. A partition member may include predetermined openings for the attachment of a suture.

The valve repair device is attached to the diseased valve by suturing the leaflet portion to the affected leaflet and suturing the muscle portion to the affected muscle. The leaflet portion and muscle portion are constructed of cloth made from expanded polytetraflouroethylene. The chords also constructed from expanded polytetraflouroethylene. The suture position for the muscle portion is determined by positioning the valve repair device adjacent to a normal "reference" marginal chord. The valve repair device may be employed to repair the anterior leaflet or posterior leaflet of the mitral valve.

The valve repair device is attached to the diseased valve by suturing the partition member (s) of the leaflet portion to the affected leaflet and suturing the muscle portion to the affected muscle.

The valve repair device may be cut by the surgeon to eliminate unnecessary area in the leaflet, or to eliminate an excess number of chords.

BRIEF DESCRIPTION OF THE DRAWINGS

Referring to the FIGURES wherein the like elements are numbered alike in the several figures

DETAILED DESCRIPTION OF THE DRAWINGS

Figure 1:
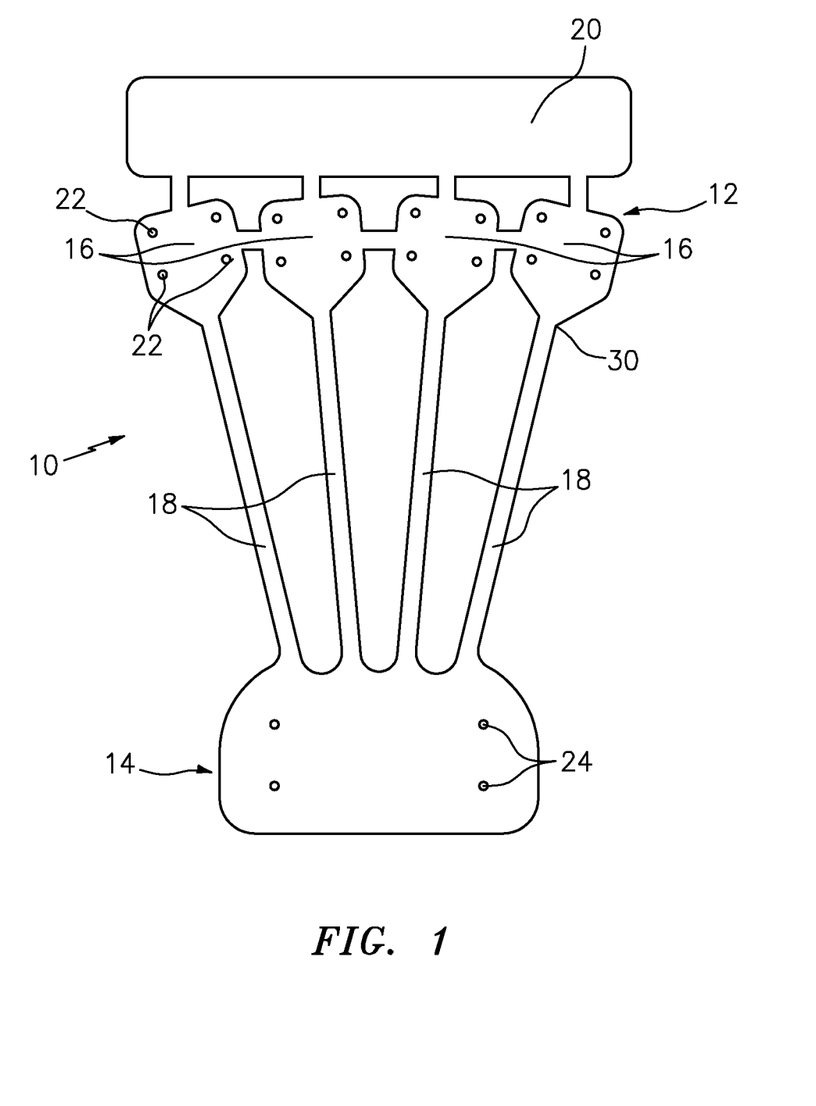
FIG. 1 shows a top view of the valve repair device.

Referring to FIG. 1, a valve repair device 10 in accordance with the present invention is illustrated. Valve repair device 10 includes a leaflet portion 12 and a muscle portion 14. The leaflet portion includes at least one partition member 16 which is attached to the leaflet of the heart. Chords 18 extend from the leaflet portion 12 and connect leaflet portion 12 to a muscle portion 14.

Valve repair device 10 is a thin flexible element preferably constructed of a biocompatible cloth. Preferably, valve repair device is constructed of a plastic reinforced cloth, such as expanded polytetraflouroethylene. Gor-Tex®, produced by W. L. Gore and Associates, Inc., Flagstaff, Ariz., is an example of a suitable biocompatible cloth made from expanded polytetraflouroethylene. Valve repair device is generally of a uniform thickness and constructed from a single sheet of biocompatible cloth. Leaflet portion 12 provides an anchor to the leaflet of a valve of the heart for chords 18, and may essentially replicate the leaflet, if the leaflet is diseased. Leaflet portion 12 is sized for repair of the anterior or posterior leaflet, and more specifically, to repair elongated or ruptured chordae of a floppy valve, either a posterior or anterior leaflet. End portion 20 may be placed in a valve repair instrument, such as the valve repair instrument disclosed in U.S. application Ser. No. 2013-0013056-A1, to aid in securing the valve repair device to the instrument. End 20 is removed as well as excess partition members 16 as needed to size the valve repair device 10 to the patient. More preferably, partition members 16 include openings 22 for suturing leaflet portion 12 to the leaflet of the heart.

Figure 2:
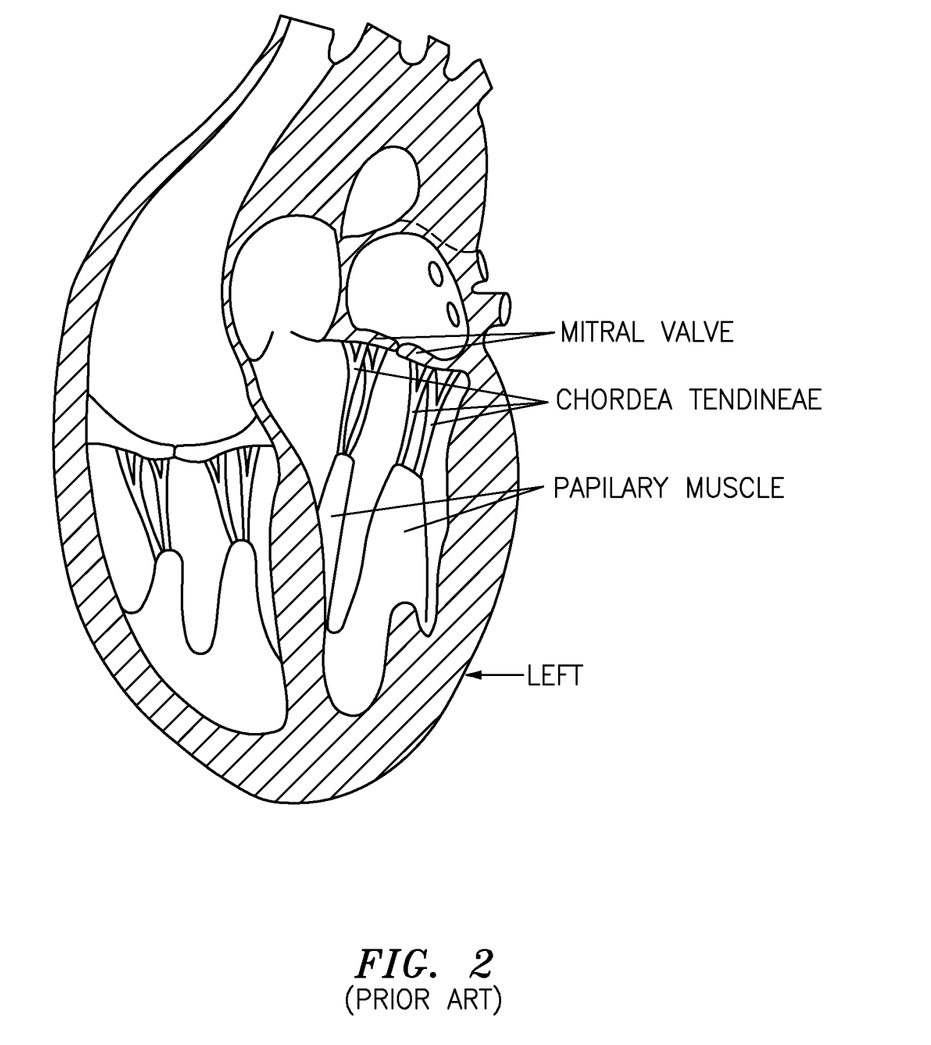
FIG. 2 illustrates a prior art cross sectional view of the heart, illustrating the mitral valve of the heart.

Muscle portion 14 may include openings 24 for suturing muscle portion 14 to the papillary muscle of the heart. Muscle portion 14 provides an anchor for chords 18 to the papillary muscle. Muscle portion 14 may be cylindrically shaped to surround the papillary muscle. Chords 18 connect leaflet portion 12 and muscle portion 14 and function as the chordae tendineae as explained in greater detail below As shown in prior art FIG. 2, the chordae tendineae are attached to the respective posterior leaflet or anterior leaflet and connect the leaflet to the papillary muscle. During a typical repair of the mitral valve, the diseased portion of the valve is excised, such as the elongated portion of a chordae or a ruptured chordae, and the remaining leaflet material is then sutured together. If the chordae tendoneae is diseased, it may also be excised, with sutures connecting the leaflet to the papillary muscle.

Figure 3:
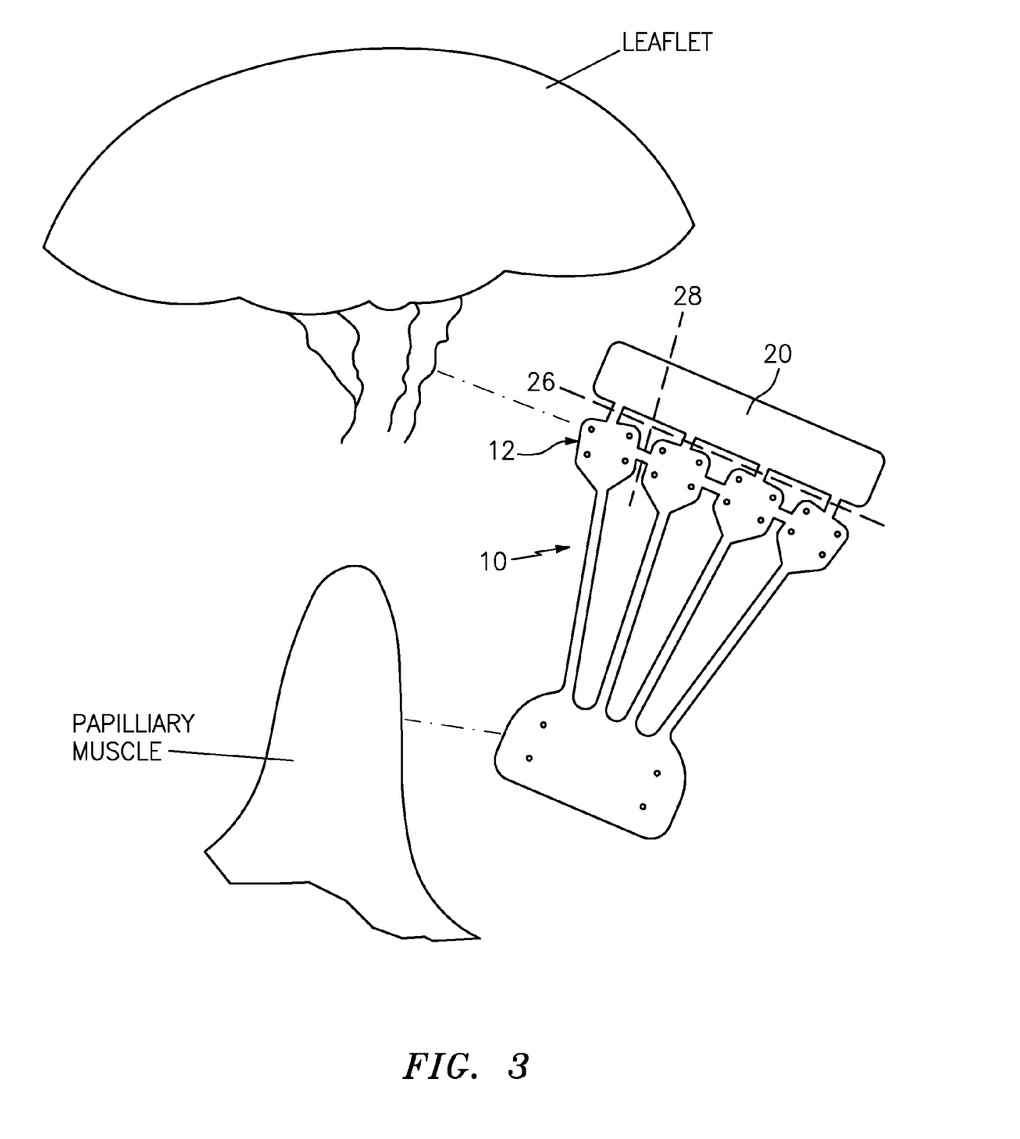
FIG. 3 shows an exploded view of the placement of the valve repair device to the repair site of an affected leaflet.
Figure 4:
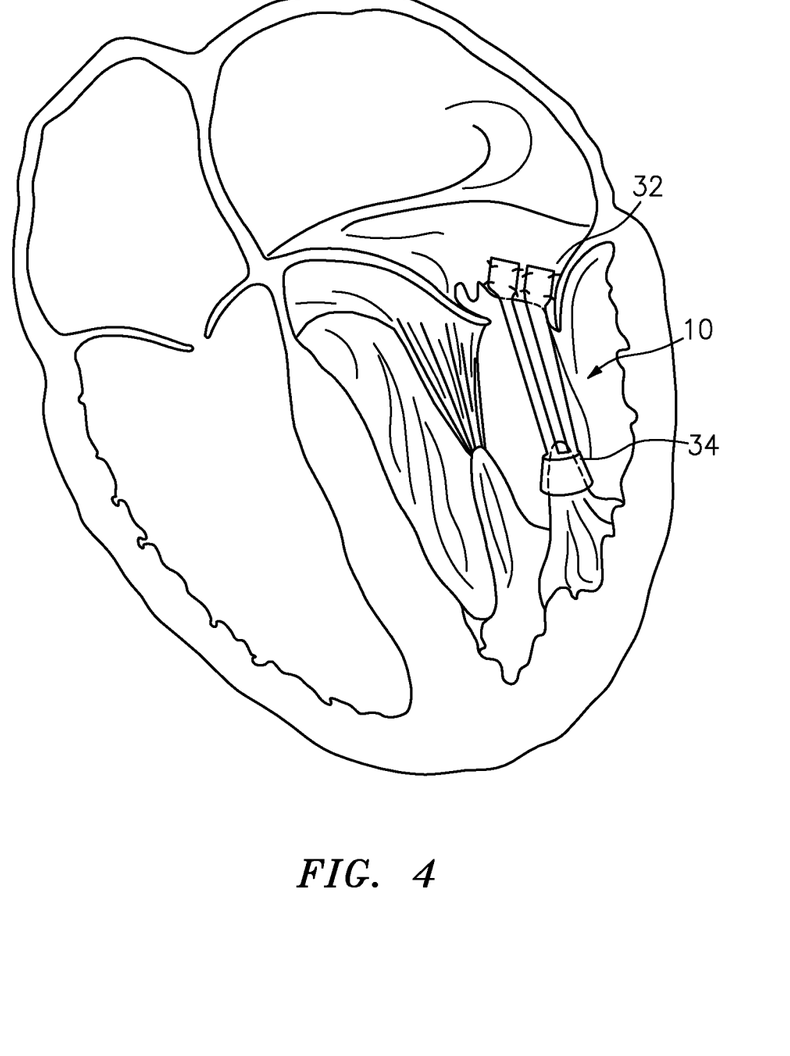
FIG. 4 shows a perspective view of the valve repair device sutured in the mitral valve.

As shown in FIGS. 3 and 4, and in accordance with the present invention, valve repair device 10 is directly sutured to the mitral valve by suturing partition members 16 of leaflet portion 12 to the affected leaflet and muscle portion 14 to the affected papillary muscle so that chords 18 replicate the chordae tendineae. End portion 20 as well as any excess partition members 16 are cut from leaflet portion 12 to an appropriate size to cover the excised diseased material, thereby reducing the impact to the leaflet and its function that is associated with the prior art method of reconnecting the leaflet at the point of excision.

During open-heart surgery, the physician will assess the degree of disease, and determine the extent of the repair to the mitral valve needed. The surgeon will first excise the diseased material, such as the elongated scallop portion of a leaflet, the perforated portion of the leaflet, the affected chordae tendineae, etc. An annular ring may be used to reinforce the mitral valve. Next, the surgeon will determine the size of the valve repair device 10 needed to effectuate the repair and may reduce leaflet 12 by cutting, such as illustrated by lines 26 and 28, unneeded partition members 16 and end portion 20 from leaflet portion 12. The physician may also cut unneeded chords 18.

The surgeon sutures leaflet portion 12 over the affected area of the posterior or anterior leaflet such that end 30 of a partition member 16 is positioned near the edge of the leaflet with suture 32. Next, the surgeon sutures muscle portion 14 to the papillary muscle with suture 34. Prior to suturing muscle portion 14 to the papillary muscle, the surgeon must determine the distance or location to position muscle portion 14 to the papillary muscle, for example as illustrated in U.S. Pat. No. 6,997,950, so that the leaflet is positioned properly to open and close effectively. Failure to accurately determine the location for muscle portion 14 may result in an ineffective repair, causing prolapse of the leaflet, which in turn may cause the valve to leak.

In order to accurately determine the location, the surgeon may estimate the needed chord length by comparing the relative length of the adjoining "reference" chords. The chordae tendeneae comprise the marginal chord, the secondary chord and the basilar chord. The marginal chord is located adjacent the margin or edge of the respective anterior or posterior leaflet. The basilar chord is located adjacent to the area adjoining the annulus of the mitral valve and the secondary chord is positioned between the marginal chord and the basilar chord. Disease in the mitral valve is typically associated with the marginal chord. Subsequent to its removal, the surgeon may approximate the needed chord length, by positioning the valve repair device adjacent to a normal marginal chord. The surgeon may also reference the chord length of the opposing anterior or posterior leaflet chordae tendeneae. Preferably, the surgeon will suture a holding stitch or a stay suture between the anterior and posterior leaflets at the level of adjoining normal chordae to obtain accurate approximation of the desired chord length. In this manner, the surgeon may suture muscle portion 14 to the papillary muscle to achieve the desired location to effectuate a repair.

Valve repair device 10 may be used to repair the anterior leaflet or the posterior leaflet, by positioning leaflet portion such that end 30 is positioned along the outer edge of the leaflet to be repaired. Moreover, valve repair device 10 may be offered in a variety of sizes and specifically in a kit form. Prior to undertaking the repair of the mitral valve, the surgeon will typically be acquainted with patient's specific physiology. During the open-heart operation, time is an important factor, and a surgeon may be confronted with an unknown defect in the valve. In use, valve repair device 10 eliminates the bulky process of affixing sutures from the papillary muscle to the respective posterior or anterior leaflet. Leaflet portion 12 is sutured directly to the leaflet using openings 22 provided in partition members 16.

The surgeon may easily modify the size of valve repair device 10 by cutting excess partition members 16 from leaflet 12 and/or cutting muscle portion 14, saving time. Moreover, the ease of attaching leaflet portion 12 to the leaflet as well as attaching muscle portion 14 to the papillary muscle increases the surgeon's ability to obtain the effective opening and closure of the valve, as the tedious and more imprecise process of attaching sutures as chords is eliminated. The anterior leaflet of the mitral valve is particularly difficult to repair given its proximity to the aortic valve. The instant invention allows the surgeon to suture leaflet portion to the anterior leaflet without affecting the aortic valve.

Figure 5:
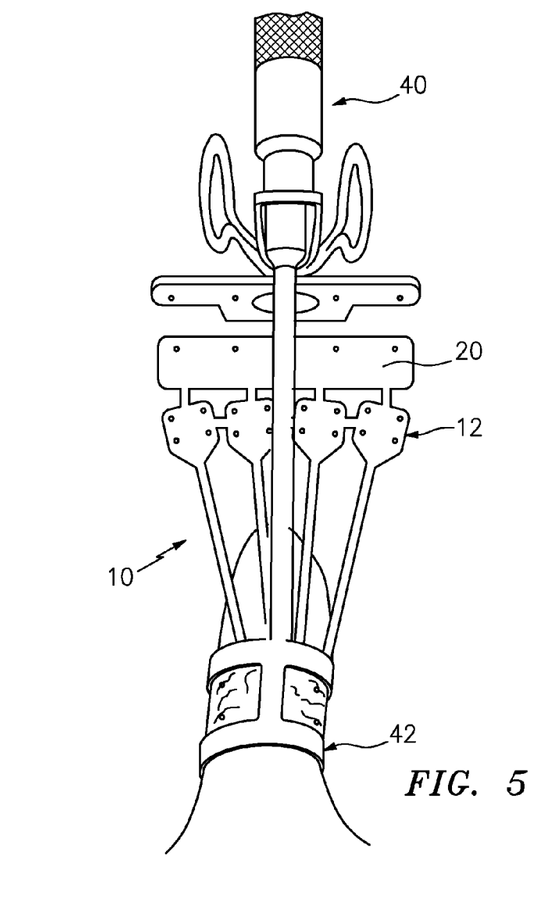
FIG. 5 shows a perspective view a perspective view of the valve repair device held by a valve repair instrument.
Figure 6:
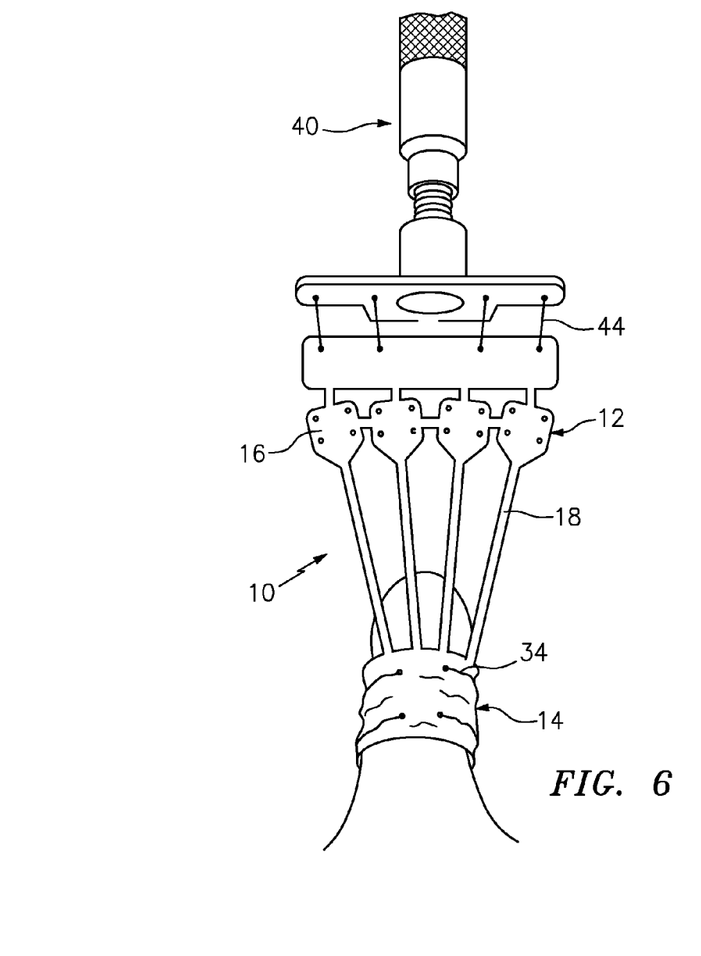
FIG. 6 shows a perspective view a perspective view of the valve repair device held by a valve repair instrument with a muscle portion sutured to the papillary muscle.

Referring now to FIGS. 5 and 6, a valve repair instrument 40, such as the valve repair instrument disclosed in U.S. application Ser. No. 2013-0013056-A1, maintains the valve repair device 10 is an expanded position. The distal end 42 of the instrument 40 is placed such that the muscle portion 14 of valve repair device 10 is adjacent to the papillary muscle. Muscle portion 14 is maintained in a semi-cylindrical shape, allowing the surgeon to place the muscle portion 14 to partially surround the papillary muscle. In this manner, the instrument is positioned such that the muscle portion 14 is positioned for suturing to the papillary muscle via sutures 34. The chords attaching the muscle portion 14 to instrument 40 (not shown) are then severed, separating the muscle portion 14 of the valve repair device 10 from the instrument 40. Leaflet portion 12 is then positioned. Excess chords 18 and partition members 16 may be cut to size valve repair device 10 as need.

Figure 7:
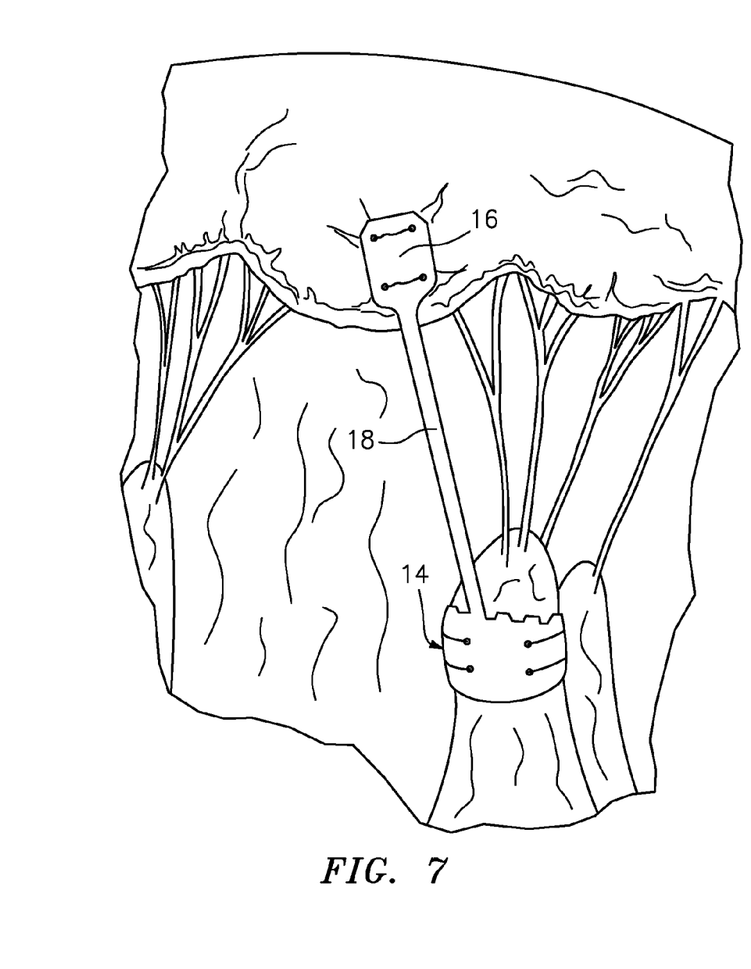
FIG. 7 shows a perspective view of the valve repair device sutured in the mitral valve using one partition member and chord.
Figure 8:
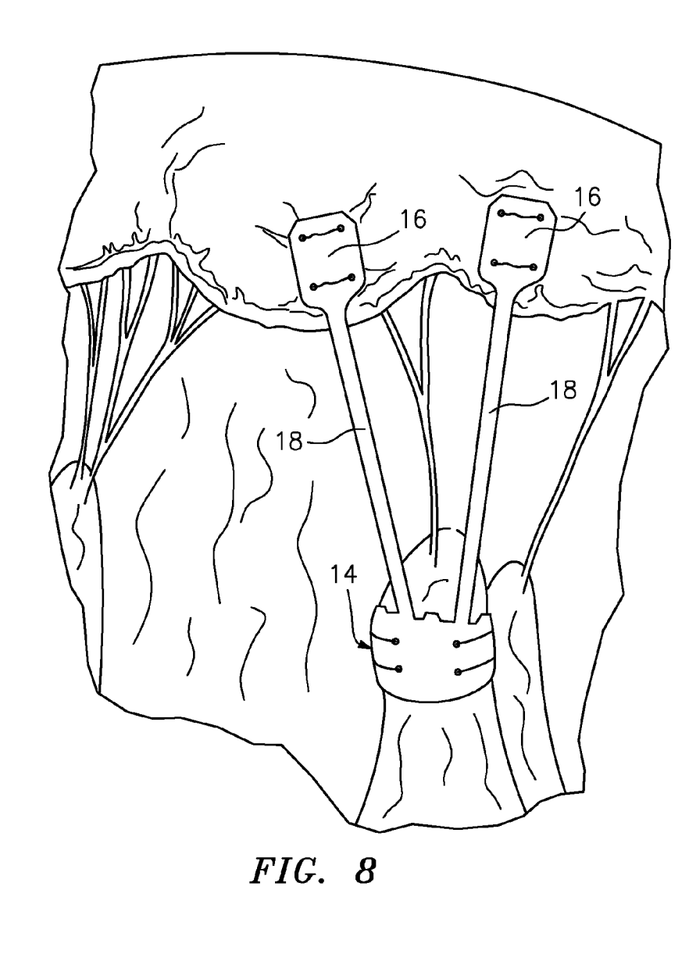
FIG. 8 shows a perspective view of the valve repair device sutured in the mitral valve using two partition members and two chords.

Turning now to FIG. 7, valve repair device 10 may be sized with a single partition member 16 of leaflet portion 12 such that a single chord 18 connects leaflet portion 12 to muscle portion 14, for example when the degree of disease and the extent of the repair is minimal. Likewise, as shown in FIG. 8, valve repair device 10 may be sized asymmetrically with two partition members 16 of leaflet portion 12 such that two chords 18 connect leaflet portion 12 to muscle portion 14, to accommodate an symmetric repair. In this manner, the number and types of repairs that may be used with the present invention is greatly enhanced. Moreover, valve repair device 10 may be offered in a variety of sizes and specifically in a kit form.

Figure 9:
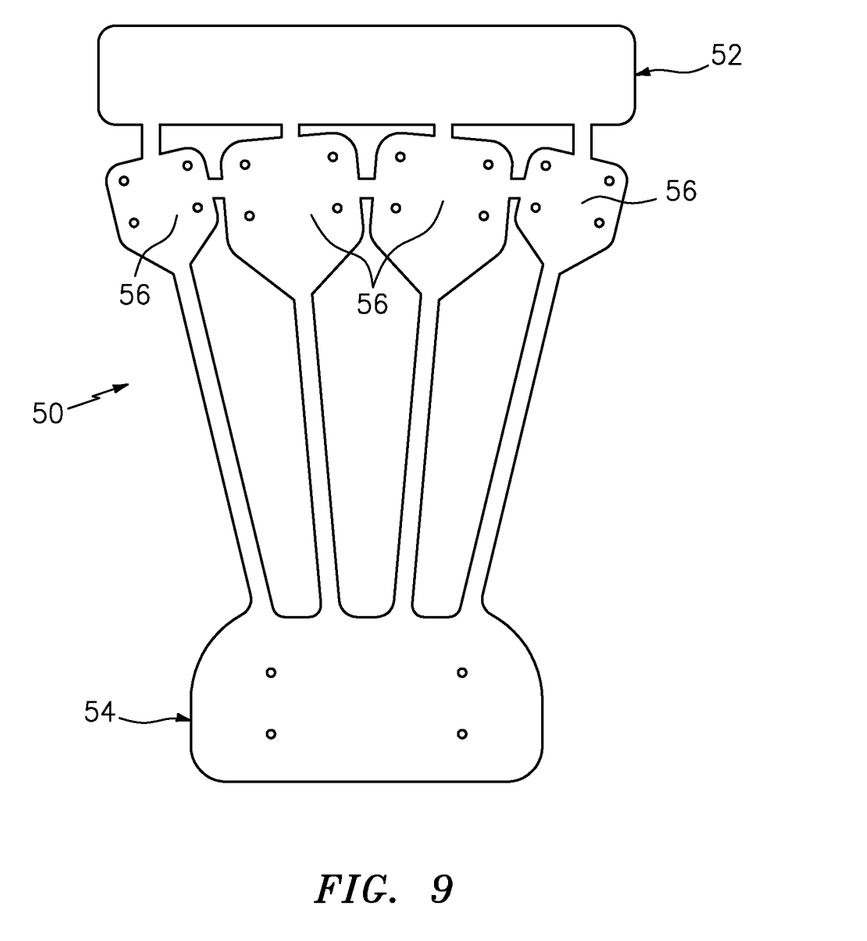
FIG. 9 shows a top view of another embodiment of the valve repair device.

Referring now to FIG. 9, another embodiment of a valve repair device 50 is illustrated. Valve repair device 50 includes leaflet portion 52 and muscle portion 54 as in the first embodiment. Is this embodiment, partition members 56 vary in size. The center partition members 56 are slightly larger than the outer partition members 56 to provide a valve repair device 56 for larger excisions.

While the invention has been described with reference to a preferred embodiment, it will be understood by those skilled in the art that various changes may be made abd equivalents may be substituted for elements thereof without departing from the scope of the invention. In addition, many modifications may be made to adapt the invention to a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A device for repair of a valve of a heart comprising:
    a flexible element, said flexible element being a single piece and being generally planar, said flexible element comprising:
    a first portion for attachment to the leaflet of the heart valve, said first portion having at least one partition member, said first portion comprising an end portion, said end portion being separable from said first portion,
    a second portion for attachment to the papillary muscle of the heart,
    at least one chord, said chord being monolithic to said flexible element and having opposed ends, one end being connected to said partition member and one end being connected to said second portion,
    a first suture for attaching said first portion to the leaflet of a heart valve, and
    a second suture for attaching said second portion to the papillary muscle of a heart.

2. The device of claim 1, wherein said flexible element comprises a cloth made from expanded polytetraflouroethylene.

3. The device of claim 1, wherein said partition member includes at least one opening for said first suture.

4. The device of claim 1, wherein said comprises flexible element comprises:
- a first portion having a plurality of partition members, and said first portion comprising an end portion, said portion being separable from said first portion, and
- a plurality of chords, each of said chords being integral to said flexible element, each of said chords having opposed ends, one end of each respective chord being attached to a respective partition member, the other end of each respective chord being attached to said second portion.

5. The device of claim 4, wherein some of the partition members may be cut from said first portion.

6. The device of claim 4, wherein said partition members vary in size.

7. The device of claim 4, wherein said second portion includes at least one opening for said second suture.

8. The device of claim 4, wherein each of said partition members have an end and are connected to said first portion along said end.

9. The device of claim 1, wherein said device is constructed of a monolithic biocompatible cloth.

10. The device of claim 1, wherein said device is constructed of a monolithic biocompatible plastic.

* * * * *